(12) United States Patent
Heaton et al.

(10) Patent No.: US 7,603,237 B2
(45) Date of Patent: Oct. 13, 2009

(54) METHOD FOR ANALYZING DATA HAVING SHARED AND DISTINCT PROPERTIES

(75) Inventors: Nicholas J. Heaton, Den Haag (NL); Jack A. La Vigne, Houston, TX (US); Ralf Heidler, Houston, TX (US); Henry N. Bachman, Missouri City, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 197 days.

(21) Appl. No.: 11/765,484

(22) Filed: Jun. 20, 2007

(65) Prior Publication Data
US 2008/0082270 A1    Apr. 3, 2008

Related U.S. Application Data (60) Provisional application No. 60/820,417, filed on Jul. 26, 2006.

(51) Int. Cl.
*G01V 1/40* (2006.01)
(52) U.S. Cl. .......................................................... 702/6
(58) Field of Classification Search ...................... 702/2, 702/6–9, 11–14, 17, 18, 39, 40, 66, 67, 73, 702/76, 100, 133, 137, 159, 166, 173, 183, 702/187, 189, 191; 175/48; 367/31, 35; 166/66.5, 248, 250.01, 250.02, 250.1, 252.1, 166/272.2, 308.3, 358; 73/152.01–152.06, 73/152.18, 152.21, 152.27–152.29, 152.35, 73/152.41–152.44, 152.56, 152.62
See application file for complete search history.

(56) References Cited

U.S. PATENT DOCUMENTS

| 4,131,875 | A | * | 12/1978 | Ingram | ......................... | 367/35 |
| 4,813,028 | A | * | 3/1989 | Liu | .............................. | 367/31 |
| 6,005,389 | A | | 12/1999 | Prammer | | |
| 6,115,671 | A | | 9/2000 | Fordham et al. | | |
| 6,462,542 | B1 | | 10/2002 | Venkataramanan et al. | | |
| 6,512,371 | B2 | | 1/2003 | Prammer | | |
| 6,703,832 | B2 | | 3/2004 | Heaton et al. | | |
| 6,714,009 | B2 | | 3/2004 | Heidler | | |

(Continued)

FOREIGN PATENT DOCUMENTS

GB    2333367    7/1999

(Continued)

OTHER PUBLICATIONS

Dunn, K.J. et al., A Method for Inverting NMR Data Sets with Different Signal to Noise Ratios, SPWLA 39 Annual Logging Symposium, May 26-29, 1998.

(Continued)

*Primary Examiner*—Edward Raymond
*Assistant Examiner*—Mohamed Charioui
(74) *Attorney, Agent, or Firm*—Darla P. Fonseca; Jaime Castano; Dale Gaudier (57) ABSTRACT

A method to determine formation properties using two or more data sets in which the solutions corresponding to the data sets represent shared and distinct formation properties. The method analyzes the data sets and computes distributions for the shared and distinct formation properties from which the formation properties are determined.

19 Claims, 6 Drawing Sheets

U.S. PATENT DOCUMENTS 6,808,028 B2 * 10/2004 Woodburn et al. ............ 175/48
2004/0169511 A1 9/2004 Minh et al.
2005/0040822 A1 2/2005 Heaton

FOREIGN PATENT DOCUMENTS

GB 2338068 12/1999
WO WO02/071100 9/2002

OTHER PUBLICATIONS

Freedman, R. et al., Field Applications of a New Nuclear Magnetic Resonance Fluid Characterization Method, SPE 71713, Sept. 30-Oct. 3, 2001, New Orleans, LA.

Freedman, R. et al., A New NMR Method of Fluid Characterization in Reservoir Rocks: Experimental Confirmation and Simulation Results, SPEJ, Dec. 2001, pp. 452-464.

Freedman, R. et al., A New Method of Fluid Characterization in Reservoir Rocks: Experimental Confirmation and Simulation Results, SPE 63214, Oct. 1-4, 2000, Dallas, Texas.

Heaton, N. et al., Saturation and Viscosity from Multidimensional Nuclear Magnetic Resonance Logging, SPE 90564, Sept. 26-29, 2004, Houston, Texas.

Sun et al., A Global Inversion Method for Multi-Dimensional NMR Logging, Journal of Magnetic Resonance, 2005, pp. 152-160.

* cited by examiner

METHOD FOR ANALYZING DATA HAVING SHARED AND DISTINCT PROPERTIES

This application claim priority to and the benefit of U.S. Provisional Application No. 60/820,417, filed Jul. 26, 2006.

BACKGROUND

Current generation unclear magnetic resonance (NMR) logging tools such as Schlumberger's MR SCANNER™ make multiple measurements in which several acquisition parameters are varied. The parameters are varied to induce changes in the NMR response that are analyzed and interpreted in terms of fluid and/or rock properties. Typically, wait times (WT) and echo spacings (TE) are varied. For all measurements, a train of echoes is measured, which constitutes the raw NMR signal. Analysis of the echo train decays provides distributions of transverse relaxation times, $T2$. Monitoring the changes in echo train amplitude with different WT allows one to determine the longitudinal relaxation times, $T1$. Similarly, variations in decay rates and echo train amplitudes with different TE allow us to measure molecular diffusion rates, $D$.

Provided that enough measurements are acquired with an appropriate range of acquisition parameters, it is possible to perform a simultaneous inversion of all data to derive 3-dimensional distributions in $T2$-$T1$-$D$ space. This approach is currently employed in MR SCANNER™ and CMR™ fluid characterization measurement and interpretation. The advantages of using a simultaneous inversion rather than separate evaluation of $T2$, $T1$, and $D$ distributions are (i) improvement in precision, and (ii) reduction in number of measurements and therefore total time required to extract the full distributions.

In addition to WT and TE variations, certain NMR logging tools acquire data at different frequencies. The effect of changing frequency is to change the depth of investigation (DOI) of the NMR measurement. For example the MR SCANNER™ tool has volumes of investigation that form thin (~1-3 mm) area in front of the antenna. The distance of the arc from the antenna face depends on frequency. A lower frequency corresponds to an arc farther from the antenna. Since the tool is run eccentered with the antenna pressed against the borehole wall, a lower frequency implies a deeper depth of investigation.

Two opposing strategies have been adopted for evaluating data acquired at different frequencies (i.e., different DOIs). The first strategy involves combining data from all DOIs and performing a single inversion. This approach is used to improve precision on a single set of answers and is appropriate provided the fluid distribution does not vary over the range of DOIs accessed during the measurements. Combining or averaging data acquired at different frequencies could lead to inconsistent datasets and erroneous interpretation if fluid distributions vary with DOI. Results obtained with MR SCANNER™ have demonstrated that fluid distributions can change substantially over the first few inches from the wellbore into the formation. The fluid variations occur because of the invasion of drilling fluid filtrate into the formation. The invading drilling fluid (filtrate) displaces movable native fluids, both water and hydrocarbon. In view of these observations, a second strategy has been adopted for MR SCANNER™. Sufficient measurements are acquired to allow independent inversion and interpretation at each DOI (i.e., at each frequency). This approach is quite general and correctly accounts for varying fluid distributions. However, it is not optimal for measurement precision. This is particularly important for the deeper DOIs (lower frequency), which typically have poorer signal-to-noise.

Several methods have been proposed to handle inversion of NMR echo decay train suites into distributions. Those methods, however, treat each experiment in a set individually or independently.

SUMMARY

The present invention includes a method to invert two or more distinct datasets in which the solutions corresponding to the distinct datasets are partially different and partially identical. The method analyzes data that measure shared and distinct properties and computes a common distribution for the shared properties and different distributions for the distinct properties. A preferred embodiment of this invention is a method for combining NMR measurements from different DOIs to improve precision at one DOI while largely maintaining the independence of fluid distributions from different DOIs. In this context, the method involves a partially constrained 4-dimensional inversion for NMR applications.

In one embodiment, the datasets are suites of NMR echo trains acquired at different DOIs. The solutions are $T2$, $T1$, $T1/T2$ and $D$ distributions (or multi-dimensional distributions), sections of which are identical for all DOIs (e.g., bound fluid volumes ("BFV") sections) while the remaining sections (free fluid volumes, "FFV") of the distributions could vary with DOI. In another embodiment, resistivity measurements from various transmitter-receiver spacings may be analyzed to determine properties such as bound fluid resistivity, free fluid resistivity, and corresponding saturations. Whether a particular property is shared or distinct depends on the circumstances of the measurement. For certain measurement-types a property may be shared, but for other measurement-types, that same property may be distinct. Shared properties are considered to be equal or otherwise related among or between relevant data sets, whereas distinct properties are considered unrelated, loosely related, or their relation is unknown between or among those data sets.

The invention allows high precision data acquired in one set of measurements (e.g., at shallow DOI) to be inverted simultaneously with lower precision data (e.g., from deeper DOI) such that the resulting multiple solutions (i.e., $T1$, $T2$, $D$ distributions from different DOIs) benefit from the high precision data while maintaining some measure of independence.

DETAILED DESCRIPTION

Today, more and more complex NMR logging tools with multiple sensors and more complicated acquisition sequences require new and more sophisticated inversion algorithms. The problem of combining different measurements to either provide more answers or increase reliability demands careful attention.

The most straightforward borehole NMR acquisition is a single echo train measured using a CPMG sequence (usually forming a phase alternated pair or PAP to address ringing). The data is inverted into an amplitude distribution with regard to transverse relaxation time T2. This problem can be written as: echo=Kernel*solution, where "echo" represents the measured echoes, "solution" is the amplitude distribution and "Kernel" is the kernel matrix of the measurement. The kernel contains the responses of the individual components in the amplitude distribution scaled to one. The equation describes the measurement as a superposition of scaled individual component responses.

In two measurements, echo1 and echo2, of the same sample are acquired (using two different sensors or acquisition sequences described by Kernel1 and Kernel2 respectively) the common solution can be found as the solution to:

$$\begin{pmatrix} echo1 \\ echo2 \end{pmatrix} = \begin{pmatrix} Kernel1 \\ Kernel2 \end{pmatrix} \text{solution},$$

which is the straightforward solution to both inversion problems.

This method, however, runs into difficulties if the two different kernels cannot fully describe the differences between the two different measurements. For instance, other parameters not part of the solution may affect the measurement as well. One problem commonly encountered (and accordingly well studied) is the common inversion of a fully polarized CPMG measurement (after a long wait time) together with a multitude of short wait time measurements (bursts), which can be repeated faster for better signal to noise. In this case the kernel for the bursts (second measurement) depends also on the polarization time and the longitudinal relaxation time (T1). Several solutions for this problem have been proposed.

The correct solution is to extend the model and include all parameters on which the kernels depend. In this case the solution would include the longitudinal relaxation time T1 as well as the transverse relaxation time T2. This leads to a two dimensional distribution. In practice, substituting the second dimension T1 with the T1/T2 ratio has been used.

Extending this same technique further to experiments with different echo spacing leads to a three dimensional inversion. In this case the kernel depends also on fluid diffusivity (via the echo spacing or the long echo spacing on the first two echoes in the diffusion editing sequence). The solution is now a three dimensional distribution with T2, T1/T2, and diffusivity as variables. Note, however, that this technique was introduced not to reconcile different measurements for common inversion of different acquisitions but rather to gain information on the additional parameter, diffusivity. The technique could be further extended to include restrictedness (degree of restriction) in time-dependent diffusion measurements.

Extending the solution to include more independent parameters allows one to gain more information from multitude of different acquisitions. However, such extension does not necessarily improve the numerical stability of the solution or improve the reliability in cases with poor signal to noise ratio. As noted earlier, combining multiple measurements in the inversion improves the stability if all measurements are sensitive to the same parameters (i.e., their kernels depend on the same parameters). If the measurements also depend on other parameters, the solution has to be extended to resolve conflicts. The present invention combines two or more acquisitions and extends the solution only partially.

Oil wells are typically drilled with drilling fluid (mud). The mud provides fabrication, conveys rock ships to the surface, and performs various other tasks. The mud weight is generally selected so that the borehole hydrostatic pressure exceeds the formation pressure, thereby containing the formation fluids while drilling. This excess pressure results in mud filtrate invading the formation close to the well bore and displacing some of the formation fluid.

In the past it has ben noted that information about invasion can be inferred by comparing NMR 3D distributions from measurements taken at multiple depths of investigation into the formation. To visualize the data, the 3D information (T2, T1, and diffusion) is typically collapsed into a 2D projection. In the examples below D-T1 maps are created from the 3D distribution. To illustrate the method of the present invention, a specific example in which the $4^{th}$ dimension is the radial distance into the formation (i.e., DOI) is presented. However, the invention is not so limited and may include an embodiment in which the $4^{th}$ dimension is not radial distance into the formation, but another dimension such as time. For example, two measurements taken a certain time apart can be analyzed in exactly the same way and the quantity would be "time variation." That would apply to combining logging while drilling—NMR with wireline—NMR measurements so that invasion differences could be accounted for.

Figure 1A:
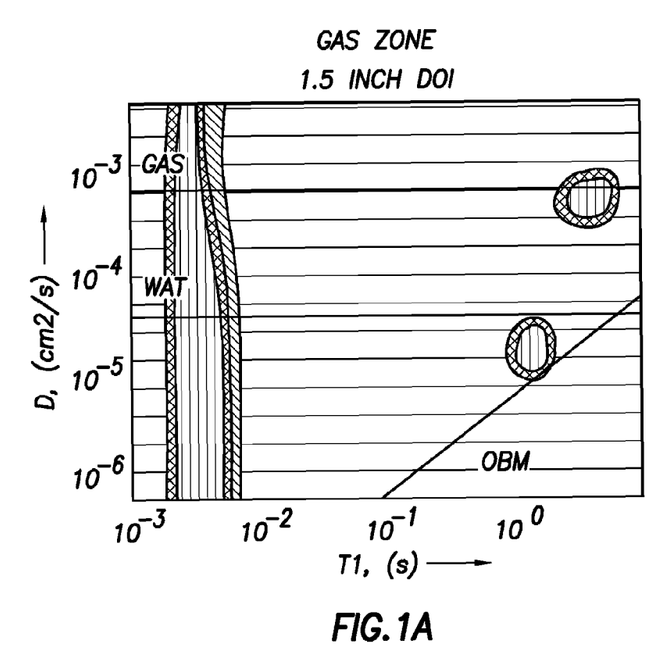
FIGS. 1A-1D are maps showing molecular diffusion rates vs. longitudinal relaxation time for shaly water and gas sands for two different depths of investigation.
Figure 1B:
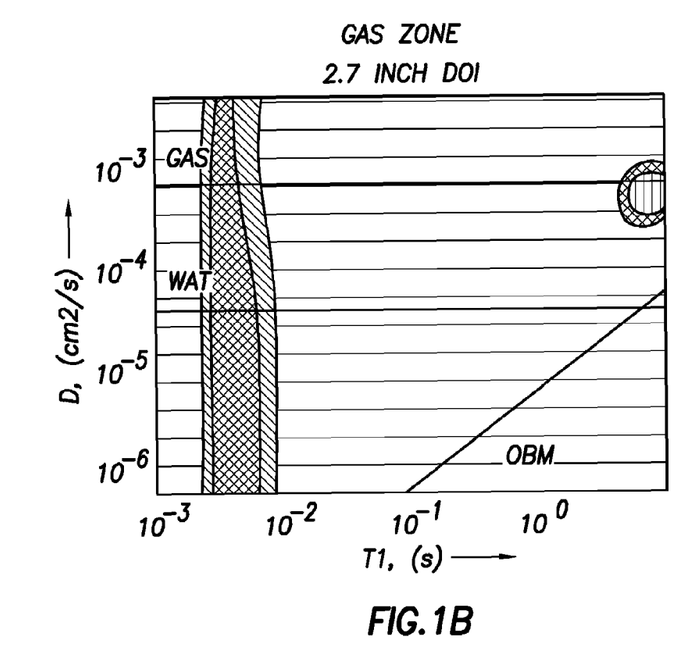
Figure 1C:
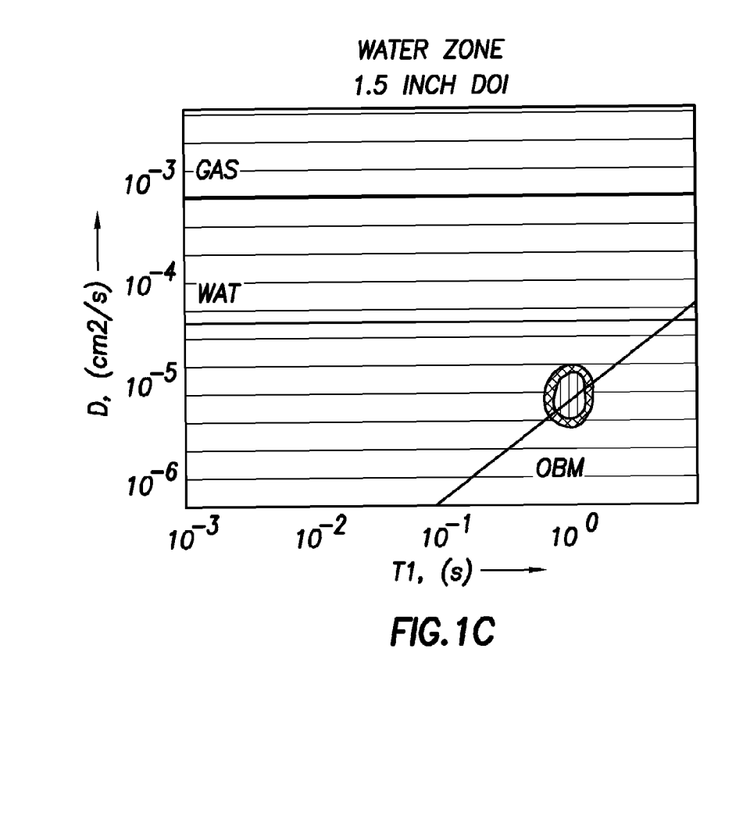
Figure 1D:
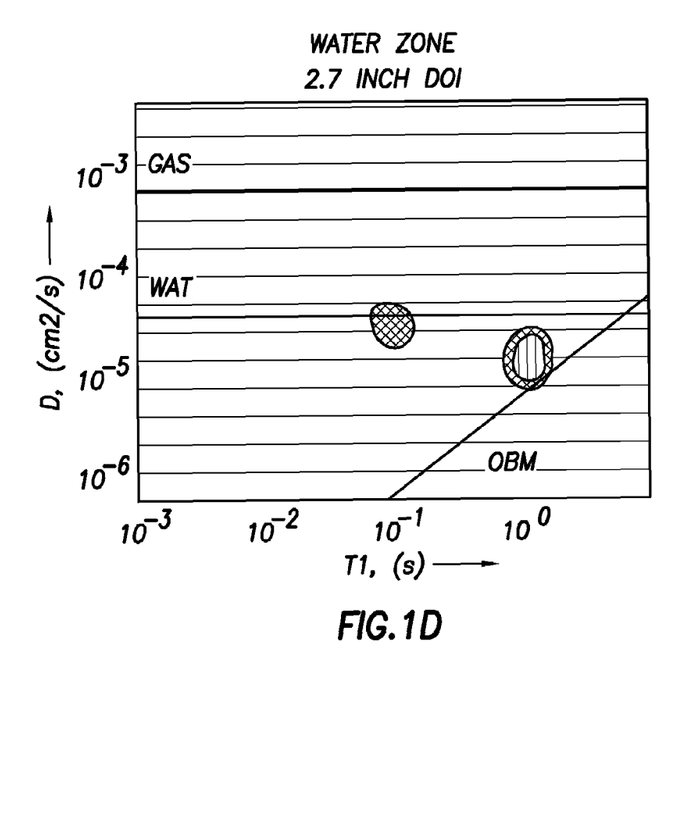
Figure 2A:
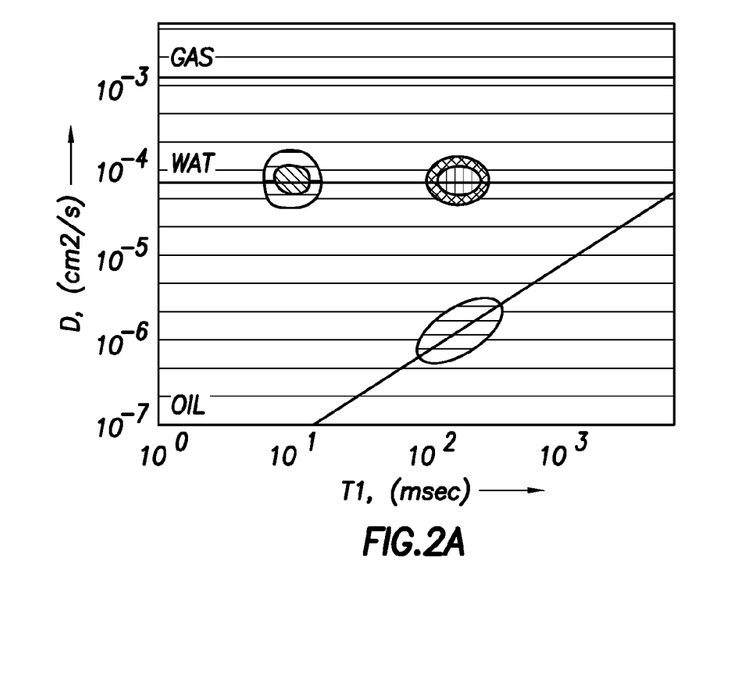
FIG. 2A is a map showing molecular diffusion rates vs. longitudinal relaxation time for depth of investigation #1 in accordance with the present invention.
Figure 2B:
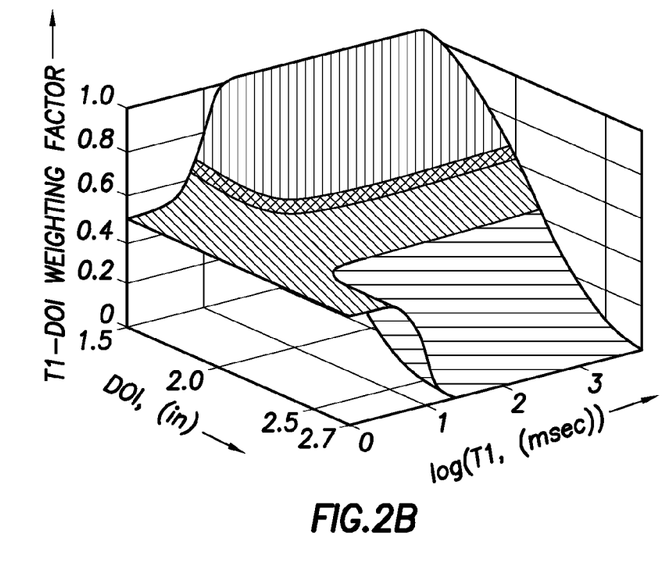
FIG. 2B is a plot showing the weighting factors used for depth of investigation #1.
Figure 2C:
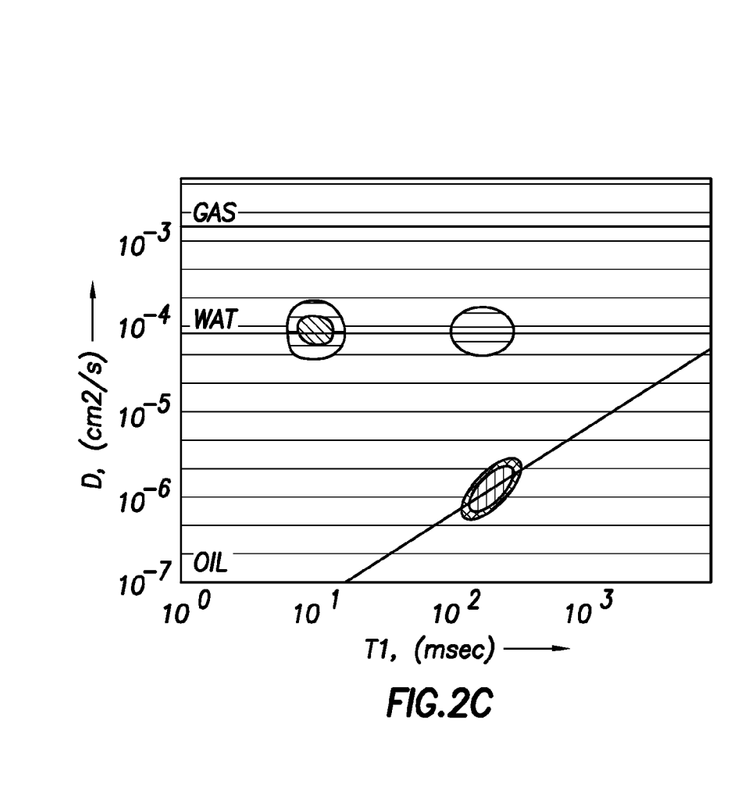
FIG. 2C is a map showing molecular diffusion rates vs. longitudinal relaxation time for depth of investigation #2 in accordance with the present invention.
Figure 2D:
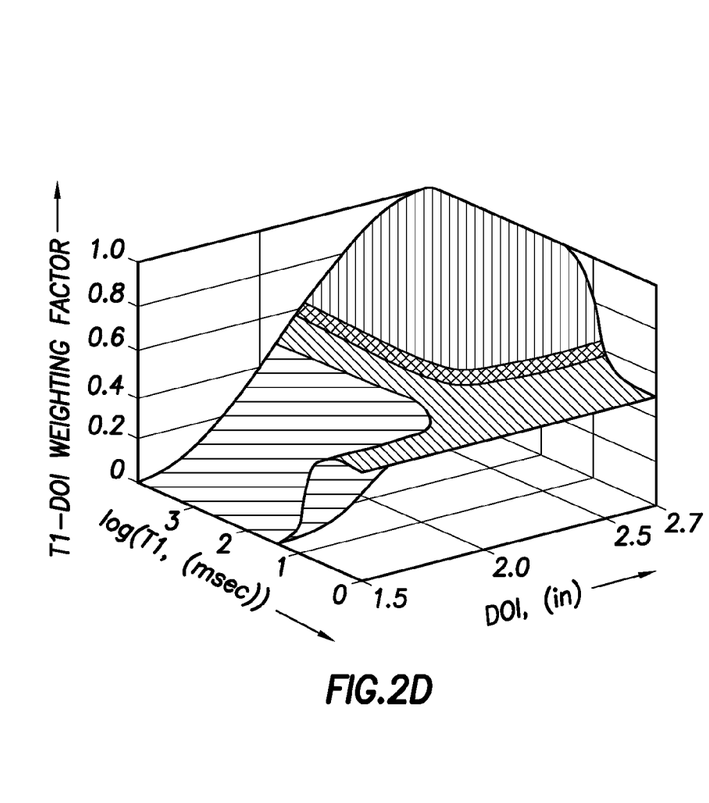
FIG. 2D is a plot showing the weighting factors used for depth of investigation #2.
Figure 3A:
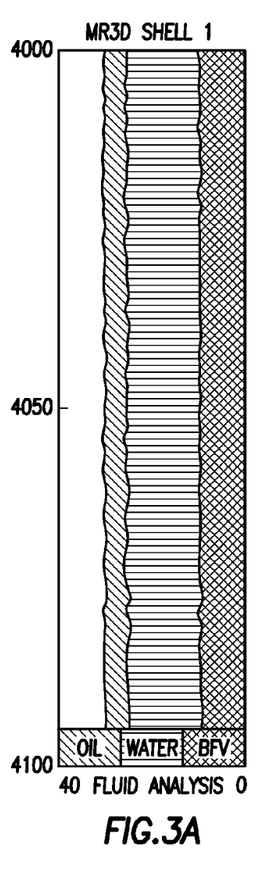
FIGS. 3A and 3B are plots showing the fluid analysis results using a standard inversion technique for depths of investigation #1 and #2, respectively.
Figure 3B:
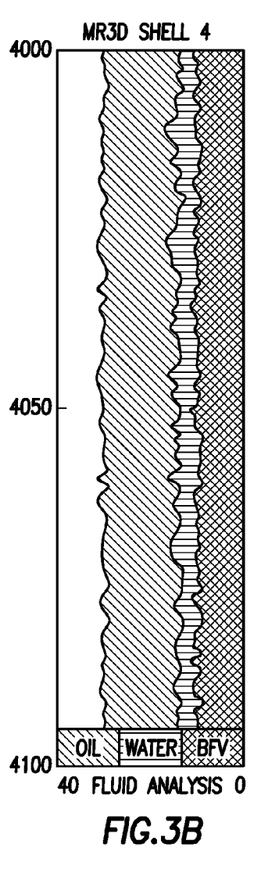
Figure 3C:
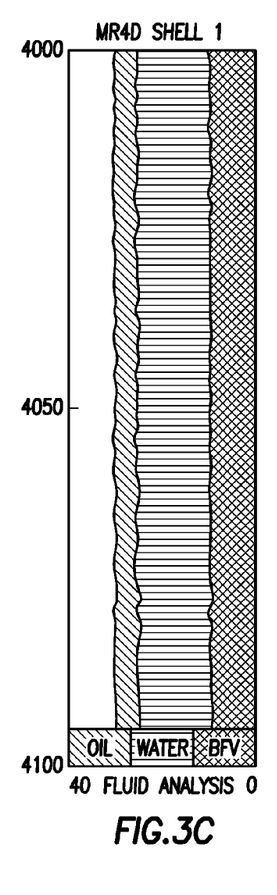
FIGS. 3C and 3D are plots showing the fluid analysis results using the inversion technique for the present invention for depths of investigation #1 and #2, respectively.
Figure 3D:
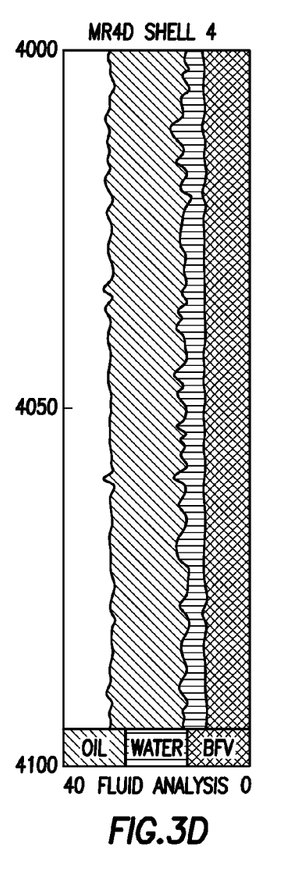
Figure 4A:
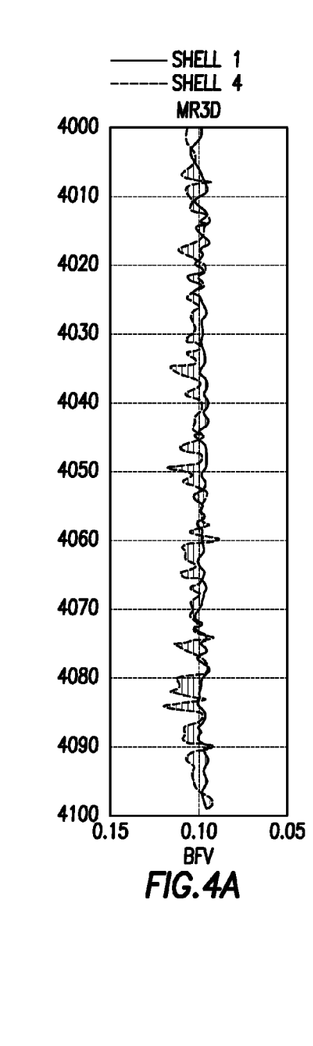
FIG. 4A is a plot showing the bound fluid volume using a standard inversion technique for depths of investigation #1 and #2.
Figure 4B:
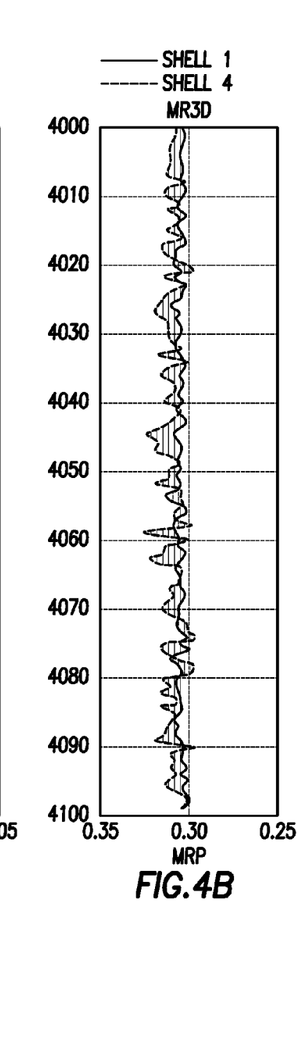
FIG. 4B is a plot showing the magnetic resonance porosity using a standard inversion technique for depths of investigation #1 and #2.
Figure 4C:
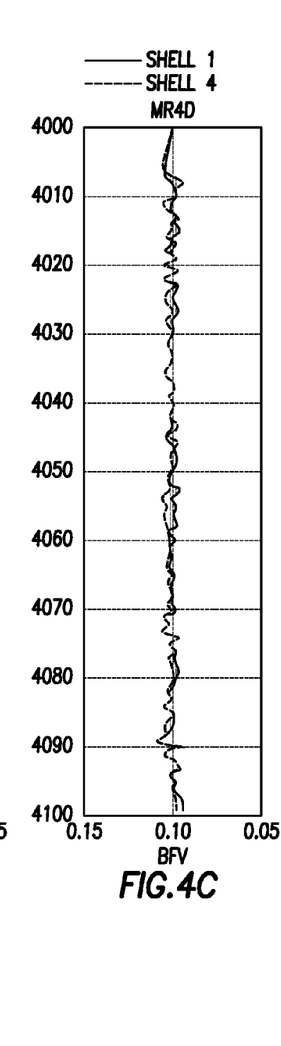
FIG. 4C is a plot showing the bound fluid volume using the inversion technique of the present invention for depths of investigation #1 and #2.
Figure 4D:
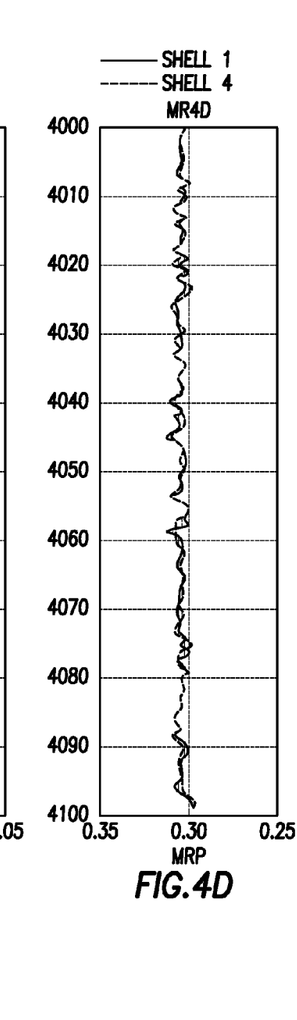
FIG. 4D is a plot showing the magnetic resonance porosity using the inversion technique of the present invention for depths of investigation #1 and #2.

The data in the example below (see FIGS. 1A-1D) was taken from shaly water and gas sands in a well drilled with an oil base mud. The leftmost D-T1 maps (FIGS. 1A and 1C) are from data taken with a DOI of 1.5 inches (Shell 1 of the MR SCANNER™) into the formation and the rightmost D-T1 maps (FIGS. 1b and 1D) are from data taken with a DOI of 2.7 inches (Shell 4 of the MR SCANNER™). The bottommost maps (FIGS. 1C and 1D) are from the water sand and the topmost maps (FIGS. 1A and 1B) are from the gas sand.

In going from 1.5 to 2.7 inches, one observes (FIGS. 1C and 1D) that the oil base mud signal decreases and the water signal increases in the water sand. Similarly, in the top maps (FIGS. 1A and 1B) one observes the oil base mud signal decreasing and the gas signal increasing as the radial depth of investigation increases.

It is well known that the strength of the NMR signal is related to the magnitude of the magnetic field strength. With oilfield NMR devices the strength of the magnetic field decreases with radius into the formation. Thus the signal to noise ratio is poorer for the deeper investigating measurements compared to the shallower. This is a motivating factor to combine the echo decay trains from the different radial depths of investigation to improve the signal to noise ratio, particularly for deeper measurements. However, the observed invasion effects indicate that the measurements should be analyzed separately. The present method increases the overall signal to noise ratio while maintaining the integrity of the radial invasion.

Typically the formation fluid will be replaced in the larger pores, leaving the fluid in smaller pores undisturbed. In the D-T1 maps shown in FIGS. 1A-1D, the regions related to changes from invasion are those regions with later T1 components (free fluid). The portions of the map that are not expected to vary radially are those regions associated with early T1 components (bound fluid).

In one embodiment of the present invention, the echo decay trains from two experiments are combined and described with a common model (solution) such that the bound fluid is shared, while the free fluid is kept distinct. By "shared" we mean there is a relationship between the particular formation property (e.g., bound water) in the two experiments, and by "distinct" we mean there is no such relationship. Normally two independent D-T1 maps are made from the data acquired with Shell 1 and Shell 4 (e.g., FIGS. 1A and 1B). Rather than creating independent maps, D-T1 distributions are created using the echo decay trains from Shell 1 and Shell 4 together. This can be done by choosing different weighting factors for bound fluids. and free fluids in Shells 1 and 4. Upon inversion, two distributions will be created using the chosen weighting factors.

The particular weighting factors may be chosen such that:
(1) the weight applied to Shell 1 data and Shell 4 data is 0.5 for the bound fluid for each distribution. The net result is that the bound fluid in the two distributions is identical and computed using all of the data from both experiments; and
(2) the weight applied to Shell 1 data equals one for the free fluid from the Shell 1 distribution and zero for the free fluid from the Shell 4 distribution. Similarly, the weight applied to Shell 1 data is zero for the free fluid from the Shell 4 distribution and one for the free fluid from the Shell 4 distribution. The net result is that the free fluid from the Shell 1 distribution is computed using the Shell 1 data and the free fluid from the Shell 4 distribution is computed using the Shell 4 data.

Thus the two distributions have independent free fluids, but identical bound fluids. The signal to noise ratio is dramatically increased for the bound fluid with a small but positive effect on the free fluid. Note the weighting factors for the bound fluid were equal in this example, but the invention is not so constrained.

Mathematically this procedure can be written as:

$$\begin{pmatrix} echo1 \\ echo2 \end{pmatrix} = \begin{pmatrix} W1*Kernel1 & W2*Kernel1 \\ W2*Kernel2 & W1*Kernel2 \end{pmatrix} \begin{pmatrix} sol1 \\ sol2 \end{pmatrix}$$

Here echo1 and echo2 describe the echo data of Shell 1 and Shell 4. W1 and W2 are diagonal matrices with the weighting functions described above in the main diagonal. Kernel1 and Kernel2 are the measurement kernels for shells 1 and 4, respectively. Note that these may differ since their respective acquisition parameters (e.g., echo spacing and gradient) may differ. The solution consists of the two parts: sol1 and sol2. This solution can be computed using a standard inversion with, for example. Tikhonov regularization or using the prior art maximum entropy inversion. For each individual shell, the solution can be written as:

$$sol\_sh1 = W1*sol1 + W2*sol2$$

and $$sol\_sh4 = W2*sol1 + W1*sol2.$$

Since the weighting functions W1 and W2 are identical for the bound fluid volume region, both solutions will be identical in that region. However, both solutions can be distinct in the free fluid volume region.

Note that this method can be easily expanded to a common inversion of three shells or other combinations of measurements (e.g., main antenna Shell 3 and high resolution antenna of the MR SCANNER™). Note further that the cut-off time in T2 for the transition can be chosen differently and does not necessarily have to coincide with the T1 or T2 cut-off time for bound fluid volume. The underlying assumption is that the response for both shells is identical for fluids with a T1 or T2 shorter than the cutoff, whereas it may vary for fluids with longer relaxation times. In practice, the cutoff will be chosen on the basis of the anticipated invasion profile and/or the mud relaxation times.

To further illustrate the method, a synthetic data set was created. Echo decay trains using the acquisition parameters shown in Table 1 were created.

TABLE 1

NMR Sequence Parameters

| Shell 1 | | | | Shell 4 | | | |
|---|---|---|---|---|---|---|---|
| Wait (sec) | TE Long (μsec) | Number Echoes | Number Repeats | Wait (sec) | TE Long (μsec) | Number Echoes | Number Repeats |
| 8.2360 | 450 | 1002 | 1 | 8.1847 | 600 | 752 | 1 |
| 2.3930 | 450 | 802 | 1 | 2.4824 | 600 | 602 | 1 |
| 1.1659 | 2000 | 800 | 1 | 1.1413 | 3000 | 600 | 1 |
| 1.1697 | 3000 | 800 | 1 | 1.1457 | 5000 | 600 | 1 |
| 1.1757 | 5000 | 800 | 1 | 1.1477 | 7000 | 600 | 1 |
| 1.1817 | 8000 | 800 | 1 | 1.1517 | 10000 | 600 | 1 |
| 1.1937 | 12000 | 800 | 1 | 1.1577 | 16000 | 600 | 1 |
| 0.8004 | 450 | 700 | 2 | 0.8006 | 600 | 512 | 1 |

TABLE 1-continued

NMR Sequence Parameters

| | Shell 1 | | | | Shell 4 | | |
|---|---|---|---|---|---|---|---|
| Wait (sec) | TE Long (μsec) | Number Echoes | Number Repeats | Wait (sec) | TE Long (μsec) | Number Echoes | Number Repeats |
| 0.1004 | 450 | 192 | 2 | 0.1006 | 600 | 144 | 2 |
| 0.0324 | 450 | 64 | 2 | 0.0326 | 600 | 64 | 2 |
| 0.0084 | 450 | 16 | 32 | 0.0086 | 600 | 16 | 32 |

Formation volumes with associated NMR properties shown in Table 2 were used to create the data.

TABLE 2

Input Fluids

| Fluid | Fluid volume Shell 1 (v/v) | Fluid volume Shell 4 (v/v) | T1 (msec) | Diffusion (cm2/sec) |
|---|---|---|---|---|
| Bound Water | 0.10 | 0.10 | 10 | 5.05e−05 |
| Free Water | 0.15 | 0.05 | 200 | 5.05e−05 |
| Oil | 0.05 | 0.15 | 200 | 1.26e−06 |

One hundred realizations were created with 2 and 4 pu/echo of random Gaussian noise applied to Shell 1 and Shell 4, respectively.

The echo decay trains were then run through an inversion process land the resulting 3D maps analyzed for porosity and fluid content. The results of the inversion are shown in FIGS. 2A-2D. The data shown in FIGS. 2A-2D are synthetic and portray an oil sand invaded with water-base mud filtrate. The bound fluid is the leftmost bright spot on the water line. The mud filtrate is the rightmost bright spot on the water line. Formation oil is the bright spot on the oil line.

The free fluid changes from more to less as one goes from distribution #1 (FIG. 2A) to distribution #2 (FIG. 2C) with a corresponding increase in formation oil. The bound fluid is shared in both distributions.

The distribution weighting factor plays an important role in this analysis. In this example, there are two weighting factors, one for each distribution. The weighting factors have depth of investigation on one axis and the common logarithm of T1 on a second axis. The amplitude of the weighting factor is shown in the Z-axis. (See FIGS. 2B and 2D)

To compare to prior art, the inversion was done twice. The first item Shell 1 and Shell 4 data were computed independently using the exiting MR3D. The second time the method for analyzing NMR experiments with shared and distinct properties was applied using MR4D. The results are shown in FIGS. 3A-3D and FIGS. 4A-4D.

Visually it is easy to see that the Shell 4 (track 2) answers computed independently (MR3D) have the largest standard deviation. It turns out that the bound fluid is the largest contributor to the standard deviation. It is clear that answers computed using a shared bound fluid (MR4D) for all depths of investigation have less variability. Table 3 shows the standard deviation of the bound fluid, free fluid, oil, and total porosity.

TABLE 3

Statistical Results

| | Standard Deviation | | | |
|---|---|---|---|---|
| | MR3D | | MR4D | |
| Volume | Shell 1 | Shell 4 | Shell 1 | Shell 4 |
| Bound Water | 0.25 | 0.68 | 0.26 | 0.33 |
| Free Water | 0.25 | 0.56 | 0.26 | 0.36 |
| Oil | 0.20 | 0.81 | 0.23 | 0.74 |
| Total Porosity | 0.29 | 0.70 | 0.27 | 0.38 |

An interesting way to look at the results is to compare the bound fluid and total porosity from Shell 1 to those same quantities in Shell 4 (FIGS. 4A-4D). This shows clearly that the bound fluid results are quite different when analyzed independently and similar when the method for analyzing NMR experiments with shared and distinct properties is applied.

Although the examples given above refer specifically to NMR-type measurements, the method of the present invention may be extended to other measurement techniques such as resistivity, sonic, nuclear, dielectric, and seismic logging. For example, for resistivity logging, the shared formation properties may be the resistivity of the native formation or the resistivity of the drilling fluid, and the distinct formation properties may be the resistivity of the invasion zone for various depths of investigation. The distributions of the drilling fluid resistivity and native formation resistivity may be constants, whereas the distribution of the invasion zone is multivalued. In general, a distribution can be single or multivalued. Shared and distinct formation properties can include, for example, shear waveform, compressional waveform, stoneley waveform, stoneley permeability, shear modulus, bulk modulus, poisson's ratio, sonic porosity, and fracture properties.

What is claimed is:

1. A method to determine earth formation properties using a logging tool disposed in a wellbore penetrating the formation, comprising
    obtaining two or more data sets using the logging tool, wherein the data sets comprise measured shared and distinct formation properties;
    computing from the data sets a common distribution for each shared formation property and a distinct distribution for each distinct formation property; and
    determining the formation properties using the common distributions and/or the distinct distributions.

2. The method of claim 1 wherein the computing includes performing an inversion using the shared and distinct sets of measurements.

3. The method of claim 2 wherein the inversion is simultaneously performed using some or all of the two or more data sets.

4. The method of claim 2, wherein the performing includes partially combining solutions for the different data sets.

5. The method of claim 1 wherein the computing includes using weighting factors to scale responses of the shared and distinct formation properties.

6. The method of claim 5 wherein the weighting factors have a functional dependence.

7. The method of claim 1 wherein the data sets depend on one or more measurement parameters selected from the group consisting of time, wait time, echo spacing, field gradient, polarization, depth of investigation, magnetic field strength, frequency, signal to noise ratio, sampling rate, and pulse sequence.

8. The method of claim 1 wherein the logging tool is a nuclear magnetic resonance tool, a resistivity tool, a sonic tool, a nuclear tool, a seismic tool, or any combination of those tools.

9. The method of claim 1 wherein the shared and distinct formation properties comprise bound fluid, free fluid, wettability, longitudinal relaxation time, transverse relaxation time, diffusivity, restrictedness, hydraulic permeability, and NMR porosity.

10. The method of claim 1 wherein the shared and distinct formation properties comprise native resistivity, invasion zone resistivity, and drilling fluid resistivity.

11. The method of claim 1 wherein the shared and distinct formation properties comprise volume of solid constituents, non-moveable and moveable fluids, and density and neutron porosity.

12. The method of claim 1 wherein the shared and distinct formation properties comprise shear waveform, compressional waveform, stoneley waveform, stoneley permeability, shear modulus, bulk modulus, poisson's ratio, sonic porosity, and fracture properties.

13. The method of claim 1 wherein the shared formation properties are considered to be equal or otherwise related among or between relevant data sets, and the distinct formation properties are considered unrelated, loosely related, or their relation is unknown among or between their corresponding data sets.

14. The method of claim 1 wherein the common and distinct distributions are plotted as functions of time, transverse relaxation time, diffusivity, longitudinal relaxation time, and radial distance from the wellbore.

15. A method to determine earth formation properties using a logging tool disposed in a wellbore penetrating the formation, comprising:
   obtaining two or more data sets using the logging tool, wherein the data sets comprise measured shared and distinct formation properties;
   using weighting factors to scale responses of the shared and distinct formation properties;
   performing an inversion using the shared and distinct sets of measurements; and
   computing from the data sets a common distribution for each shared formation property and a distinct distribution for each distinct formation property;
   determining the formation properties using the common distributions and/or the distinct distributions.

16. The method of claim 15 wherein the weighting factors have a functional dependence.

17. The method of claim 15 wherein the inversion is simultaneously performed using some or all of the two or more data sets.

18. The method of claim 15, wherein the performing includes partially combining solutions for the different data sets.

19. The method of claim 15 wherein the logging tool is a nuclear magnetic resonance tool, a resistivity tool, a sonic tool, a nuclear tool, a seismic tool, or any combination of those tools.

* * * * *